(12) United States Patent
Yasui et al.

(10) Patent No.: US 9,557,220 B2
(45) Date of Patent: Jan. 31, 2017

(54) FOURIER TRANSFORM SPECTROSCOPY METHOD, SPECTROSCOPIC DEVICE, AND SPECTROSCOPIC MEASUREMENT PROGRAM THAT IMPROVE SPECTRAL RESOLUTION AND SPECTRAL ACCURACY

(71) Applicant: Osaka University, Osaka (JP)

(72) Inventors: Takeshi Yasui, Tokushima (JP); Mamoru Hashimoto, Osaka (JP); Tsutomu Araki, Osaka (JP); Yuki Iyonaga, Osaka (JP)

(73) Assignee: Osaka Univeristy, Osaka (JP)

( * ) Notice: Subject to any disclaimer, the term of this patent is extended or adjusted under 35 U.S.C. 154(b) by 88 days.

(21) Appl. No.: 14/423,765

(22) PCT Filed: Aug. 26, 2013

(86) PCT No.: PCT/JP2013/005031
§ 371 (c)(1),
(2) Date: Feb. 25, 2015

(87) PCT Pub. No.: WO2014/034085
PCT Pub. Date: Mar. 6, 2014

(65) Prior Publication Data
US 2015/0204722 A1    Jul. 23, 2015

(30) Foreign Application Priority Data

Aug. 26, 2012 (JP) ................................. 2012-185978

(51) Int. Cl.
*G01J 3/453*    (2006.01)
*G01N 21/3581*    (2014.01)
(Continued)

(52) U.S. Cl.
CPC .............. *G01J 3/453* (2013.01); *G01J 3/2889* (2013.01); *G01J 3/42* (2013.01); *G01N 21/3581* (2013.01);
(Continued)

(58) Field of Classification Search
CPC ............ G01J 3/453; G01J 3/42; G01J 3/2889; G01J 2003/0281; G01J 2003/283; G01N 21/3581; G01N 21/3586; G01N 2021/3595
(Continued)

(56) References Cited

U.S. PATENT DOCUMENTS 5,748,309 A    5/1998    van der Weide et al.
7,605,371 B2    10/2009    Yasui et al.

FOREIGN PATENT DOCUMENTS

JP    2011-099752 A    5/2011
JP    2011-242180 A    12/2011
WO    2006-092874    9/2006

OTHER PUBLICATIONS

Yasui. Super-resolution discrete-fourier-transform spectroscopy using precisely periodic radiation beyond time window size limitation, 2014, https://arxiv.org/ftp/arxiv/papers/1412/1412.3822.pdf.*

(Continued)

*Primary Examiner* — David Porta
*Assistant Examiner* — Gisselle Gutierrez
(74) *Attorney, Agent, or Firm* — Ogilvie Law Firm

(57) ABSTRACT

Provided is a Fourier transform spectroscopy method that removes restrictions on spectral resolution and spectral accuracy in Fourier transform spectroscopy for observing a cyclic repeating phenomenon, that realizes, theoretically, infinitesimal spectral resolution accuracy. After accurately and sufficiently stabilizing the repetition period of a phe-
(Continued)

(1) Temporal waveform (2) Amplitude spectrum nomenon, a temporal waveform is acquired by making a repetition period and a time width for observing the temporal waveform of a phenomenon strictly conform, and by performing a Fourier transform, acquired is a discrete separation spectrum in which the inverse number of the observation time window size T is made a frequency data gap. Measurement is repeated while causing the repetition period to change, and the gap of the discrete separation spectrum is supplemented. Thereby, in a case of an observation target in which the existence time of a phenomenon is longer than the repetition period, the spectral resolution of the obtained discrete separation spectrum becomes infinitesimal.

16 Claims, 12 Drawing Sheets

(51) Int. Cl.
*G01J 3/28* (2006.01)
*G01J 3/42* (2006.01)
*G01N 21/35* (2014.01)
*G01N 21/3586* (2014.01)
*G01J 3/02* (2006.01)

(52) U.S. Cl.
CPC ... *G01J 2003/0281* (2013.01); *G01J 2003/283* (2013.01); *G01N 21/3586* (2013.01); *G01N 2021/3595* (2013.01)

(58) Field of Classification Search
USPC .................................................. 250/339.08
See application file for complete search history.

(56) References Cited

OTHER PUBLICATIONS

Fritz Keilmann, et al., "Time-domain mid-infrared frequency-comb spectrometer", Optics Letters / vol. 29, No. 13 / pp. 1542-1544, Jul. 1, 2004.

* cited by examiner

Measurement temporal waveform *h(t)*

(1)　　　　　　　　　　(2)

(a)　　　(b)

(a)　　　(b)

FOURIER TRANSFORM SPECTROSCOPY METHOD, SPECTROSCOPIC DEVICE, AND SPECTROSCOPIC MEASUREMENT PROGRAM THAT IMPROVE SPECTRAL RESOLUTION AND SPECTRAL ACCURACY

FIELD OF THE INVENTION

The present invention relates to a Fourier transform spectroscopy method, a spectroscopic device, and a spectroscopic measurement program that improve spectral resolution and spectral accuracy.

BACKGROUND OF THE INVENTION

A Fourier transform spectroscopy method (a Fourier transform frequency analysis method) is a spectroscopic technique where spectra are obtained by measuring a temporal waveform or interferogram of electromagnetic radiation, or other types of radiation, and calculating its Fourier transform.

When a periodical signal is considered, a temporal waveform signal h(t) observed in a time domain is related with a frequency spectrum H(f) observed in a frequency domain based on the Fourier transform (Equation (1)) and the inverse Fourier transform (Equation (2)) as are shown by the following Equations.

[Equation 1]

$$H(f) = \int_{-\infty}^{\infty} h(t) \exp(-2\pi i f t) dt \quad (1)$$

[Equation 2]

$$h(t) = \int_{-\infty}^{\infty} H(f) \exp(2\pi i f t) df \quad (2)$$

Signals in a time domain and in a frequency domain are considered to be equivalent to each other from the relations of the Fourier transform and the inverse Fourier transform. Before computers became available, measurements in a frequency (or wavelength) domain were generally performed for the spectrum measurement due to a difficulty in performing the Fourier transform.

For example, in optical spectroscopy such as dispersive spectrometers, a spectrum was acquired by spatially separating multiple wavelength components of light with dispersive optical elements (a diffraction grating, a prism and so on) and selecting only a specific wavelength component.

However, the Fourier transform became extremely easy as computers became available, which made it possible to acquire the spectrum for each frequency by the Fourier transform of a measured temporal waveform of a phenomenon, namely, the Fourier transform spectroscopy.

Typical examples of the Fourier transform spectroscopy method includes a pulse Fourier-transform nuclear magnetic resonance spectroscopy method (FT-NMR), a nuclear magnetic resonance imaging method (MRI), a Fourier-transform infrared spectroscopy method (FT-IR), a terahertz time-domain spectroscopy method (THz-TDS) and so on, and these are widely used in industrial fields and medical fields. A FT-NMR irradiates pulsed high frequency radio waves (radio waves) on a sample tube set at the center of a superconducting magnet and measures a time domain signal called FID (Free Induction Decay) and consequently a NMR spectrum is acquired by the Fourier transform of this FID. A Nuclear Magnetic Resonance Imaging (MRI) applies NMR spectra to computed tomography. A FT-IR and a THz-TDS observe interferogram and electric field as a function of time, respectively, and spectra are acquired after the Fourier transform of them.

Features of a Fourier transform spectroscopy method are includes the following 1) to 4).

1) High Signal Intensity.

The signal intensity is high and hence a high signal-to-noise ratio is acquired because the whole spectral components of input signal is collected at the same time by acquiring the time-domain signal in the Fourier transform spectroscopy method.

2) Bright Optical System without Slits.

High optical throughput and a high signal-to-noise ratio can be realized because slits required in a dispersive spectrometer are not necessary and its optical system is brighter than that of dispersive spectrometer.

3) A Continuous Spectrum with High Spectral Accuracy.

Continuous spectrum can be observed and its spectral accuracy is relatively high due to Fourier transform.

4) Applicable to Various Electromagnetic Regions.

The Fourier transform spectroscopy method is now becoming the main stream of the spectroscopic measurement and is now widely used in various fields thanks to the features mentioned above.

TABLE 1

| Fourier transform spectroscopy method | Application field |
| --- | --- |
| Nuclear magnetic resonance spectroscopy method (NMR) | Structural determination of organic substances and so on |
| Nuclear magnetic resonance imaging | Biological body tomography imaging and, so on |
| Fourier transform infrared spectroscopy inspection method (FT-IR) | Semiconductor defect Drug and food analysis and so on |
| Terahertz time domain spectroscopy method (THz-TDS) | Drug analysis, Non-destructive inspection Protein identification |
| Fourier transfer mass spectroscopy method (FT-MS) | Protein identification |
| Fourier transfer optical spectrum analyzer | Optical communication, optical device evaluation |
| Fourier transform spectrum analyzer | Electronic device evaluation |

The important characteristics of the spectroscopy are the spectral resolution and the spectral accuracy.

FIG. 1 shows a temporal waveform of an observed signal and the corresponding amplitude spectrum obtained by its Fourier transform. When the temporal waveform of a phenomenon is measured, the spectral resolution is simply determined by the inverse of the measurement time window size during which the temporal waveform is observed (an observation time window). Therefore, as the time window is increased, the spectral resolution is enhanced. On the other hand, when the phenomenon repeats, it is generally accepted that the achievable spectral resolution is limited to its repetition frequency (theoretical limit of spectral resolution) because the maximum window size is restricted to a single repetition period to avoid the coexistence of multiple signals. Also, when the majority of the signal components are temporally localized, excessive extension of the window size increases the noise contribution.

Also, the acquisition time increases in proportion to the expansion of the observation time window size. Furthermore, in the case of optical FTS, the travel range of a translation stage used for time-delay scanning practically limits the spectral resolution. The practical spectral resolution is far lower than the spectral resolution to be determined by the repetition frequency and it is not easy to realize a sufficiently large size of the observation time window. Considering such these factors, the actual observation time window size is selected, which determines the spectral resolution.

On the other hand, the spectral accuracy depends on the accuracy of time sampling in the temporal waveform.

For improving the substance identification capacity in spectroscopic analysis, further improvement of the spectral resolution and the spectral accuracy are necessary.

Some inventors among the inventors of this invention have already proposed a measurement equipment of a high speed THz spectrometry with a spectral resolution of a theoretical limit (=repetition frequency=mode-locked frequency) in the THz-TDS. (Refer to Patent Literature 1)

The present invention resolves a limitation of spectral resolution in the Fourier transform spectroscopy including the THz-TDS, realizes a theoretically infinitesimal spectral resolution (an infinite spectral resolving power) and improves a spectral accuracy remarkably.

PRIOR ART

Patent Literature

[Patent Literature 1] U.S. Pat. No. 4,565,198 B

OUTLINE OF THE INVENTION

Problems to be Solved by the Invention

As was mentioned above, further improvements of the spectral resolution and the spectral accuracy are necessary for improving the substance identification capacity in the spectroscopic analysis.

In view of the circumstance mentioned above, the present invention aims to provide a Fourier transform spectroscopy method, a spectroscopic device, and a spectroscopic measurement program that resolve a limitation of spectral resolution in the Fourier transform spectroscopy, realizes a theoretically infinitesimal spectral resolution and improves a spectral accuracy remarkably.

Means to Solve the Problems

In order to achieve the purposes mentioned above, the Fourier transform spectroscopy method according to the present invention obtains a discrete distribution spectrum with a frequency interval equal to a reciprocal of the observation time window size T by performing the Fourier transform of a temporal waveform acquired after matching a repetition period of a phenomenon with a time window size (an observation time window size T) for observing the temporal waveform of the phenomenon, in the Fourier transform spectroscopy method (the Fourier transform frequency analysis method) for observing a periodical and repetitive phenomenon.

For each plot of the discrete distribution spectrum above, the Equation 3 below holds with $f_n$ as the frequency of each plot and n as the degree (integer).

[Equation 3]
$$f_n = \frac{n}{T} \qquad (3)$$

As shown above, in a case wherein a relaxation time of an observation phenomenon is longer than a repetition period, the spectral resolution of the acquired discrete distribution spectrum becomes infinitesimal (the spectral resolving power becomes infinite) and thus improves the spectral accuracy.

In the Fourier transform spectroscopy, by strictly fitting an observation time window size T with a repetition period after stabilizing a repetition period of a phenomenon precisely and thoroughly, the upper limit of spectral resolution of the Fourier transform spectroscopy (determined by a repetition frequency) is resolved and a theoretically infinitesimal spectral resolution is realized.

It is excusable to obtain a temporal waveform coinciding with a repetition period by introducing null data for the acquired temporal waveform data so that the resulting temporal waveform data coincides with repetition period after acquiring a temporal waveform by an observation within a shorter time than a repetition period instead of letting the observation time window size T mentioned above coincide with the repetition period. However, it should be noted that the repetition period must be strictly coincided with the data after completion. In this case, the accuracy of the Fourier transformation spectrum may be degraded due to defects of temporal waveform in null-data interpolation portion compared with the acquirement of temporal waveform by fitting the a repetition period with an observation time size T.

It is more preferable for the Fourier transformation spectroscopy method according to this invention as mentioned above to be further comprising a step for changing repetition periods, a step for obtaining a discrete distribution spectrum after Fourier transformation of the acquired temporal waveform after changing a repetition periods and a step for overlaying multiple discrete distribution spectra of different repetition cycles.

A fine spectrum is acquired by complementing gaps between each plot of a discrete distribution spectrum acquired by changing the repetition periods (or frequencies). Also, not only spectral resolution but also spectral accuracy is remarkably improved by stabilizing the repetition period accurately and thoroughly.

Here, it is preferable to stabilize the repetition period by referencing a frequency standard. The repetition period can be stabilized accurately and thoroughly by referencing a frequency standard.

Also, it is more preferable to acquire discrete distribution spectra by the discrete Fourier transform of the digitized temporal waveform data corresponding to one repetition period acquired either by gitizing the temporal waveform data by the time interval of 1/integer of the repetition period, or setting the period of the repetition phenomena at an integer multiple of the digitizing time interval of the temporal waveform data. The Fourier transform spectrum accuracy can be improved.

The Fourier transform spectroscopy method of the present invention as described above is preferably used for the terahertz time-domain spectroscopy method (THz-TD). For this application, two femtosecond lasers with different laser pulse repetition frequencies (mode-locked frequencies) are employed as light sources for the terahertz time region spectroscopy method. Each mode-locked frequency of the 2 femtosecond lasers is accurately and thoroughly stabilized by referencing a frequency standard and two femtosecond lasers are simultaneously and independently controlled so that the mode-locked frequency difference is kept at a constant value. And, the output light of one femtosecond laser is used as a pumping light for generating THz and the output light of other femtosecond laser is used as a probe pulse light for THz detection.

By this, a pulse period which is a repetition period can be stabilized.

The Fourier transform spectroscopy method of the present invention as described above is preferably applied to the Fourier transform infrared spectroscopic device for conducting the Fourier transformation Infrared spectroscopy method (FT-IR). For this application, two femtosecond lasers with different laser pulse repetition frequencies (mode-locked frequencies) are employed. Each mode-locked frequency and carrier-envelope-offset frequency and carrier-envelope-offset frequency of the 2 femtosecond lasers is accurately and thoroughly stabilized by using a frequency standard and two femtosecond lasers are simultaneously and independently controlled so that the mode-locked frequency difference is kept at a constant value. And, the output light of one femtosecond laser is used for generation of infrared light for sample measurement and the output light of other femtosecond laser is used for a local oscillator light in heterodyne interferometer.

By this, a repetition period can be stabilized.

The configuration disclosed in the literature shown below employs not the homodyne interference utilizing incoherent infrared light source (ceramic light source, Tungsten-Halogen light source, Tungsten-Iodine lamp and so on), but heterodyne interference by an coherent infrared light generated by 2 femtosecond lasers and a nonlinear optical crystal, and can be used in the Fourier transform spectroscopy method as mentioned above for the present invention.
(Literature)
F. Keilmann, C. Gohle and R. Holzwarth, "Time-domain mid-infrared frequency-comb spectrometer" Optics Letters, Vol. 29 Issue 13, pp. 1542-1544 (2004)

The Fourier transform spectroscopy method of the present invention as describe above is preferably applied to one of the Fourier transform spectroscopy methods such as the nuclear magnetic resonance spectroscopy (NMR) method, the nuclear magnetic resonance imaging (MRI) method, the Fourier transform mass spectrometric analysis (FT-MS), the optical or electrical Fourier transform spectrum analyzer because they obtain the spectra by observing the temporal waveform of repetitive phenomena and performing their Fourier transform.

Next, the Fourier transform spectroscopic device according the present invention is explained.

The Fourier transformation spectroscopic device according to the present invention is equipped with, in the Fourier transform spectroscopic device for observing a periodical and repetitive phenomenon, means to acquire a temporal waveform by coinciding the repetition period of a phenomenon with the time window size for observing a temporal waveform of the phenomenon (an observation time window size T) and means to acquire a discrete distribution spectrum with a frequency interval equal to a reciprocal of the observation time window size T by the Fourier transform of the acquired temporal waveform.

By such a configuration, the spectral resolution of the acquired discrete distribution spectrum becomes infinitesimal (the spectral resolution power becomes infinite) in the case of a phenomenon with a longer relaxation time than the repetition period and the spectral accuracy can be improved.

For each plot of the discrete distribution spectrum above, the Equation 3 above holds with $f_n$ as a frequency of each plot and n as an order (integer).

Here, it is preferable for the Fourier transform Spectroscopic device to be further equipped with means for changing repetition period and means for overlaying multiple discrete distribution spectra of different repetition periods.

The spectral resolution can be remarkably improved by acquiring fine spectra after interleaving additional marks in gaps between each plot of the discrete distribution spectra acquired by changing the repetition frequencies. Also, the spectral accuracy can be also remarkably improved by stabilizing the repetition period accurately and thoroughly.

The Fourier transform spectroscopic device of the present invention as described above is preferably used as the terahertz time-domain spectroscopic device for conducting the terahertz time-domain spectroscopy method (THz-TDS).

For this application, two femtosecond lasers with different laser pulse repetition frequencies (mode-locked frequencies) are employed as light sources for the terahertz time-domain spectroscopy method.

Each mode-locked frequency of the 2 femtosecond lasers is accurately and thoroughly stabilized by referencing a frequency standard and two femtosecond lasers are simultaneously and independently controlled so that the mode-locked frequency difference is kept at a constant value. And, the output light of one femtosecond laser is used as a pumping light for generating THz and the output light of other femtosecond laser is used as a probe pulse light for THz detection.

By this, a repetition period can be stabilized.

The Fourier transform spectroscopy method of the present invention as described above is preferably applied to the Fourier transform infrared spectroscopic device for conducting the Fourier transformation infrared spectroscopy method (FT-IR).

For this application, two femtosecond lasers with different laser pulse repetition frequencies (mode-locked frequencies) are employed.

Each mode-locked frequency and carrier-envelope-offset frequency of the 2 femtosecond lasers are accurately and thoroughly stabilized by referencing a frequency standard and two femtosecond lasers are simultaneously and independently controlled so that the mode-locked frequency difference is kept at a constant value.

And, the output light of one femtosecond laser is used for an IR light for sample measurement and the output light of other femtosecond laser is used for a local oscillator light in heterodyne interferometry.

By this, a repetition period can be stabilized.

Next, a Fourier transformation spectroscopic measurement program according to the present invention is explained.

The Fourier transformation spectroscopic measurement program according to the present invention is the Fourier transformation spectroscopic measurement program for observing periodical and repetitive phenomena, equipped with means to acquire a temporal waveform by coinciding the repetition periods of a phenomenon with the time window size for observing the temporal waveform of the phenomenon (an observation time window size T) and means to acquire a discrete distribution spectrum with as a frequency interval equal to a reciprocal of the observation time window size T by the Fourier transform of the acquired temporal waveform.

By this program, the spectral resolution of the acquired discrete distribution spectrum becomes infinitesimal (the spectral resolving power becomes infinite) in the case of a phenomenon with a relaxation time longer than the repetition period and the spectral accuracy can be improved.

Note that for each plot of the discrete distribution spectrum above, the Equation 3 above holds with $f_n$ as a frequency of each plot and n as a degree (integer).

Here, the Fourier transform Spectroscopic measurement program according to the present invention mentioned above is preferably equipped further with means for changing repetition periods and means for overlaying multiple discrete distribution spectra of different repetition periods and is preferably designed to let a computer operate these means.

Not only the spectral resolution but also the spectral accuracy can be remarkably improved by acquiring fine spectra after interleaving additional marks in gaps between each plot of discrete distribution spectra acquired by changing the repetition frequencies.

The Fourier transform spectroscopic measurement program according to the present invention mentioned above is suitably mounted in the Fourier transformation spectroscopy devices such as the nuclear magnetic resonance spectroscopic (NMR) device, the nuclear magnetic resonance imaging (MRI) device, the terahertz time-domain spectroscopic (THz-TDS) device, the Fourier transform infrared spectroscopic (FT-IR) device, the Fourier transform mass spectrometric analysis (FT-MS), the electrical or optical Fourier transform spectrum analyzer.

Each equipment mentioned above is for observing repetition phenomena and the spectral resolution and the spectral accuracy can be improved.

Effects of the Invention

The present invention is effective in resolving the limitation of the spectral resolution and the spectral accuracy of the Fourier transformation spectroscopy method, realizing the theoretically infinitesimal spectral resolution and remarkably improving the spectral accuracy.

When the present invention is utilized, the performance of the Fourier transformation spectroscopy methods such as the nuclear magnetic resonance spectroscopy (NMR) method, the optical or electrical Fourier transform spectrum analyzer are remarkably improved without a drastic modification of the hardware. Improvement of the spectral resolution and the spectral accuracy in the Fourier transform spectroscopy method enhance the identification ability of various materials and lead to higher performance of various instruments. As a result, application of the device in the fields of semiconductor and analytical chemistry is further promoted. Also, there is a possibility of the enhanced finer spatial resolution in computed tomographic images in the field of the nuclear magnetic resonance spectroscopy (MRI) wherein FT-NMR is applied to the computed tomography.

BEST MODE FOR CARRYING OUT THE INVENTION

Embodiments of the present invention will be described in detail below with reference to the drawings. The present invention is not limited to the following embodiment and examples of shown in the figure, and the present invention can be variously changed in design.

(The Principle of the Present Invention)

Figure 2:
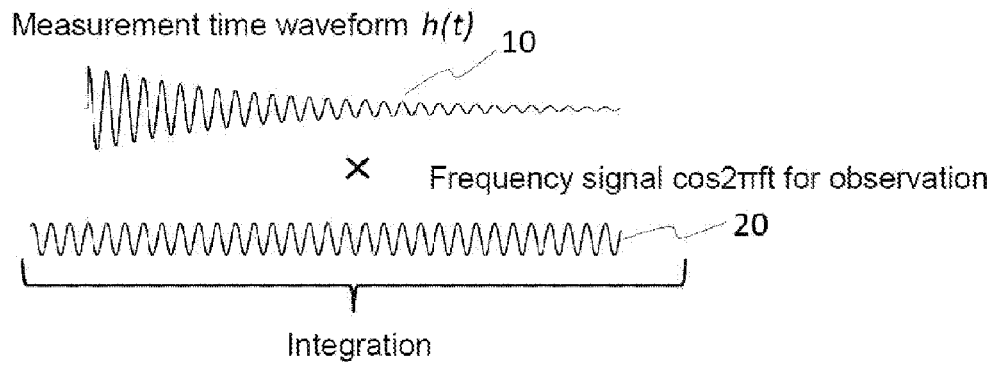
FIG. 2 An explanatory drawing of the Fourier transform of an acruired temporal waveform FIG. 3 An image figure of observing the temporally overlapped multiple signals with a relaxation time longer repetition period as repetition phenomena by precisely periodic radiation FIG. 4 An image figure of signal acquisition of portions of signals with different timings with a time window size FIG. 5 An explanatory drawing of Fourier transform of portions of the phenomenon with different timings FIG. 6 An explanatory drawing of temporal connection of portions of signals with different timings and Fourier transform of the temporally connected signal without limitation of the time window size.

First we consider the measured temporal waveform h(t) of a phenomenon and its FT spectrum H(f) given by Equation (1). This equation indicates that a spectral component H(f)

is obtained by multiplying h(t) by a frequency signal exp (−2 π ift) and then integrating the product for an infinite integration period. This process is illustrated in FIG. 2, where cos 2 π ft is shown as the real part of exp(+2 π ift). Furthermore, the whole spectrum can be acquired by performing the similar process to each frequency component. Here, the spectral resolution is determined by integration period, corresponding to the observation time window size.

Although the integration period (observation time window size) has to be increased to improve the spectral resolution, the practical resolution is limited by the achievable finite integration period due to the SNR, the acquisition time, and/or the stage travel range.

Next we consider the case where h(t) is made to repeat by using precisely periodic pulsed radiation with a repetition period (for example, free induction decay in NMR and so on).

Figure 3:
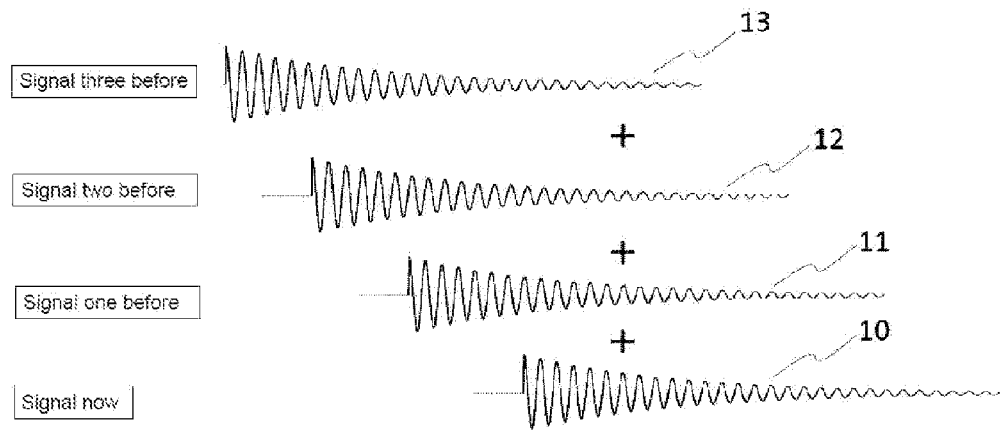

FIG. 3 shows an image figure of observing the temporally overlapped multiple signals with a relaxation time longer repetition period as repetition phenomena by precisely periodic radiation. When the relaxation time of h(t) is longer than T, a series of signals h(t) temporally overlap, each subsequent event (the signal now 10, the signal one before 11, the signal two before 12 and the signal three before 13) being delayed by an integer multiple of T.

Figure 4:
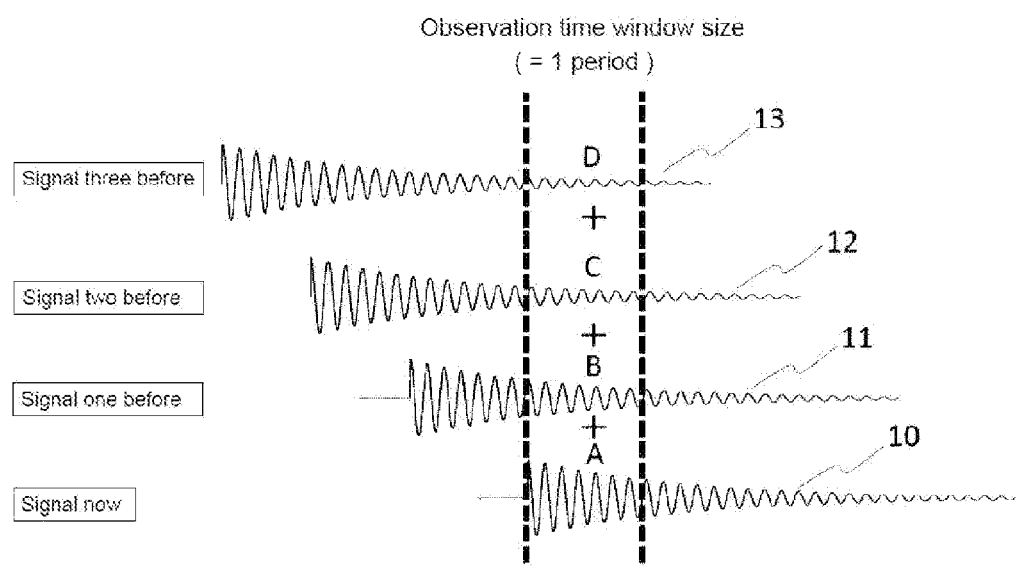

When such temporally overlapped signals are observed with an observation time window size of 1 cycle, the time-domain (A) of the relaxation phenomenon by the pulse signal now 10, the time-domain (B) of the relaxation phenomenon by the pulse signal one before 11, the time-domain (C) of the relation phenomenon by the pulse signal two before 12 and the time-domain (D) of the relation phenomenon by the pulse signal three before 13 become included in the observation time window size as shown in FIG. 4.

Figure 5:
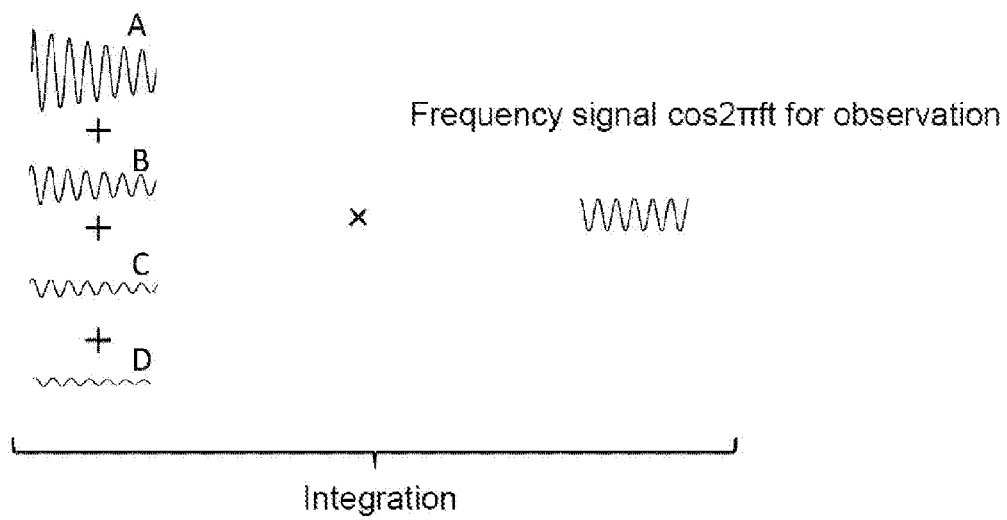
Figure 6:
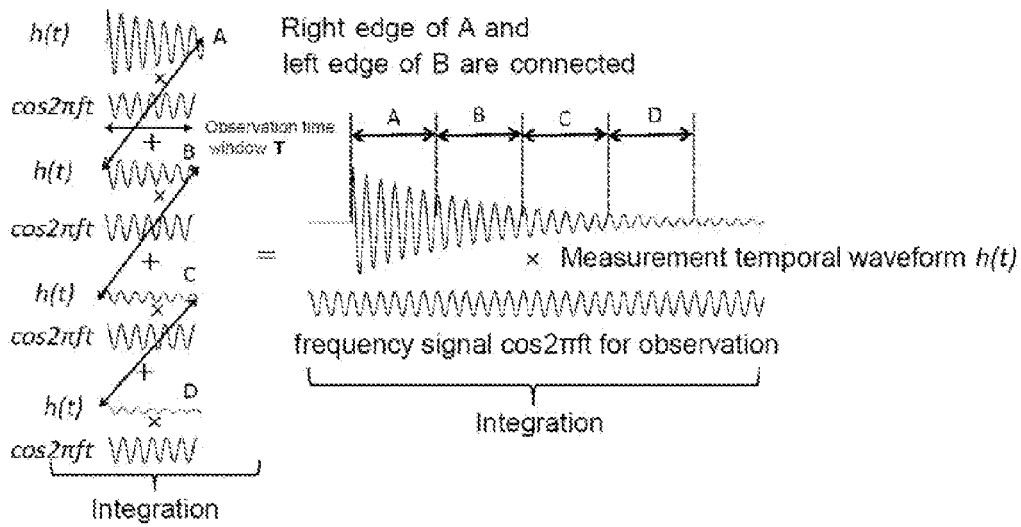

As shown in FIG. 5, the temporal integration of the multiplication of the sum of each relaxation signal included in the time domain (A), (B), (C) and (D), and the frequency signal cos(2π ft) which is to be preferably observed provides a Fourier transform spectrum of a repetition phenomenon observed within 1 cycle.

Here, when a repetition cycle of the light source that induces the relaxation phenomenon, after being stabilized correctly and thoroughly, is measured in a manner that the repetition cycle and the observation time window size are strictly coincided, each signal included in time-domains (A), (B), (C) and (D) can be connected as a temporary continuous signal.

Namely, the above procedure becomes equivalent to measuring the signal with relaxation time long enough by an observation time window size (a time integration region) of an infinite length in spite of the fact that the repetition cycle is equal to the observation time window size.

Here, assuming the repetition cycle (the observation time window size) is T, the frequency for obtaining the spectral information by the infinitesimal spectral element resolution (the infinite spectral resolving power) is discretely distributed by an interval of 1/T and the frequency of each plot is given by the Equation (3) mentioned above. Here, $f_n$ is the frequency of each plot and n is the degree (integer) of the plot.

Figure 7:
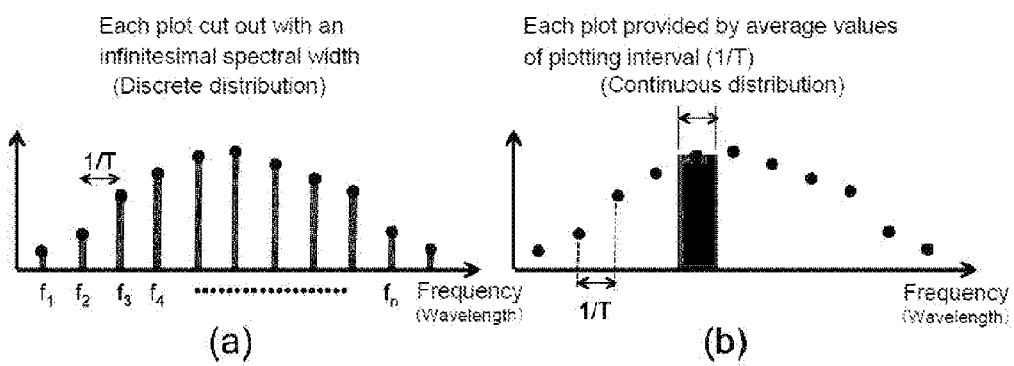
FIG. 7 A behavior of plot distribution that constitutes a spectrum (plotting interval 1/T). (a) Discrete distribution of plots cut out with an infinitesimal spectral width (in the case of the present invention), (b) Continuous distribution of plots provided by average values (in the case of a conventional method).

Also, FIG. 7 shows the circumstance of plot distribution that constitutes a spectrum (plotting interval 1/T). FIG. 7(a) shows the discrete distribution of the plot cut out with an infinitesimal spectral width (in case of the present invention) and, on the other hand, the FIG. 7(b) shows the continuous distribution of plots given by average values (the conventional method).

Next, how the discrete distribution of the plot with the infinitesimal spectral width can be obtained by sampling is explained.

When a single phenomenon h(t) is acquired by a sampling frequency more than 2 times larger than the maximum frequency of h(t), the acquired information can be discretized without loss of the information based on the sampling theorem.

The spectral acquired at the sampling frequency more than two times larger than the maximum frequency of h(t) can be expressed by the Equation (4) below by using the Fourier series expansion. Here, m is an integer and τ is a sampling interval. Here, 1/τ must be 2 times larger than the maximum frequency of h(t) to satisfy the sampling theorem.

[Equation 4]

$$H(f) = \sum_{m=-\infty}^{\infty} h(m\tau)\exp(-2\pi im\tau f) \quad (4)$$

On the other hand, overlapping of the single phenomenon by the time interval of T=Nτ results in the Equation (5) as shown below.

[Equation 5]

$$g(m\tau) = \sum_{k=-\infty}^{\infty} h(m\tau - kT) \quad (5)$$

For g(mτ) in the above Equation (5), the discrete Fourier transform using the data amount for one repetition cycle that is to say data m=0, - - - , N−1, is defined by the Equation (6) below.

[Equation 6]

$$G(f_n) = \sum_{m=0}^{N-1} g(m\tau)\exp(-2\pi if_n m\tau) \quad (6)$$

In the Equation (6) described above, $f_n$ is the Equation (3) mentioned earlier and n is an integer. The Equation (6) above can be expanded to the Equation (7) below.

[Equation 7]

$$G(f_n) = \sum_{m=0}^{N-1} \sum_{k=-\infty}^{\infty} h(m\tau - kT)\exp\{-2\pi if_n(m\tau - kT)\} \quad (7)$$
$$= H(f_n)$$

Namely, sampling of the signal by dividing the repetition cycle T of the phenomenon into N equal parts (note that N/T is preferably set at more than 2 times the maximum frequency of the phenomenon in order to satisfy the sampling theorem) or obtaining of a discrete spectrum by the discrete Fourier transform of the discrete spectrum for one cycle of a repetition cycle by setting the repetition cycle of the phenomenon at N times of the sampling interval of the temporal waveform, make each plot of the discrete spectrum equal to the observed value of the original single phenomenon obtained with the infinitesimal spectral resolution (the infinite spectral resolving power). Note that if N is an exponential of 2, the computing time can be remarkably reduced because the high speed discrete Fourier transform can be utilized.

FIG. 7 shows a fact to be noted that the spectrum being obtained with the infinitesimal spectral resolution (the infinite spectral resolving power) is due to a fact that the spectrum is discrete. This is because each plot that constitutes a conventional spectrum (a dispersion spectroscopy method, for example) is continuously distributed with an average value of the plot interval (1/T) as shown in FIG. 7(b). On the other hand, the spectral resolution of each plot (the cut out spectral width) constitutes an infinitesimal discrete distribution in the case of the present invention as shown in FIG. 7(a).

Figure 8:
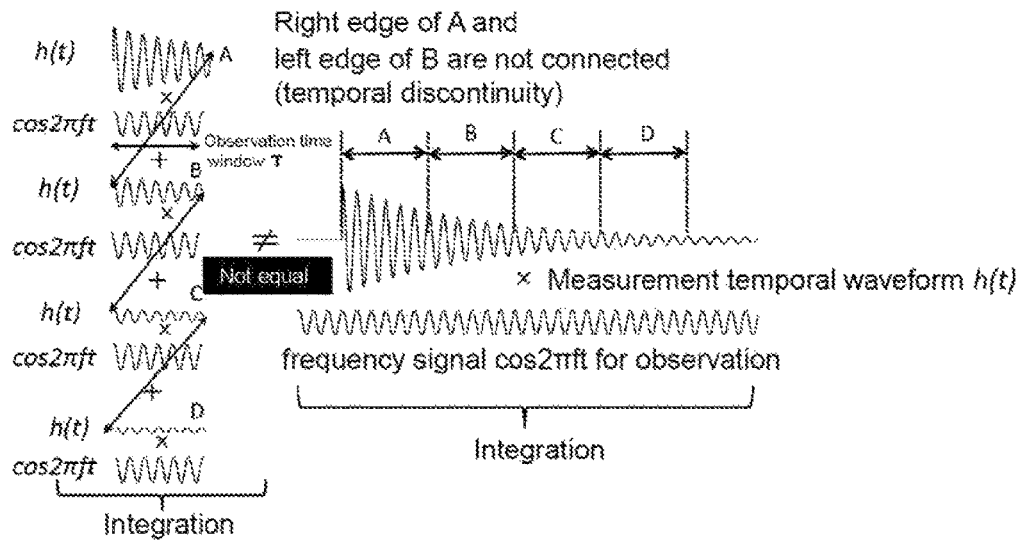
FIG. 8 An explanatory drawing for the case wherein the observation time window size is not equal to one repetition period FIG. 9 An explanatory drawing of discrete Fourier transform spectrum for the temporally connected signal and the spectral interleaving by changing repetition period.

On the other hand, if the observation time window size is not strictly equal to one cycle, each signal included in time-domains (A), (B), (C) and (D) cannot be linked as a temporally continuous signal and will be changed into a signal that includes temporal breakpoints (Refer to FIG. 8), which is not resultantly equivalent to measuring the signal of a relaxation phenomenon with an infinite observation time window size (a time integration region). Namely, if the Equation (3) is not satisfied, the correct spectrum cannot be obtained.

Each plot of the spectrum shown in FIG. 7(a) is discretely distributed though each plot possesses the infinitesimal spectral resolution (the infinite spectral resolving power). Therefore, if operated as it is, the practical spectral resolution becomes the plot interval (the reciprocal of the pulse interval 1/T).

For effectively utilizing the infinitesimal spectral resolution (the infinite spectral resolving power) possessed by each plot, it is necessary to supplement the gap part existing between two plots. To accomplish this, the successive acquiring of a spectral wave pattern in FIG. 7(a) under the change of the pulse cycle T, followed by complement of finally overlaying of the acquired spectral wave patterns leads to acquirement of a spectrum with a narrower plot interval. (Refer to FIG. 9)

This is equivalent to the measuring of discrete spectral information while changing the pulse cycle T in the Equation (3) above. As result, the spectral resolution is remarkably improved as much as to the extent of increase in practical plot numbers.

Also, as the repetition cycle of the relaxation phenomenon is stabilized correctly and thoroughly in advance referencing a frequency standard and the measurement is performed by strictly fitting the repletion cycle with the observation time window size (T), the gap of each plot is constant and the absolute accuracy of the spectral wave length (the frequency) becomes extremely accurate. As a result, better spectral resolution improves the accuracy of reading for wavelengths (the frequencies) and the spectral accuracy is also improved.

In the Embodiments below, the present invention will be explained exemplifying the Fourier transform spectroscopy method and the spectroscopic device in the THz-TD. And usefulness of the Fourier transform spectroscopy method of the present invention will be assessed by using low pressure water vapor as a sample.

[Embodiment 1]

Figure 1:
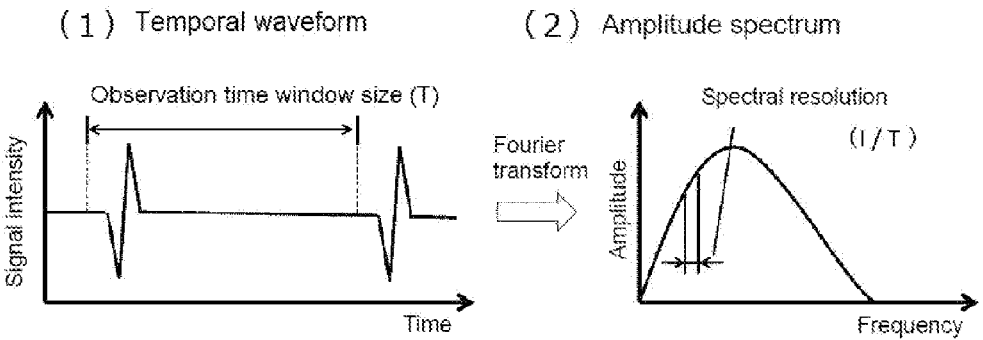
FIG. 1 An explanatory drawing of the Fourier transform spectroscopy method

A practical example of the Fourier transform spectroscopy method in the THz-TDS of the present invention is shown as embodiment 1. In the THz-TDS, after acquiring an electric field temporal waveform of a pulsate THz wave (THz pulse) that propagates the free space and consequently the amplitude spectrum is acquired by the Fourier transform as shown in FIG. 1. However, because it is impossible to directly measure (real time measurement of THz pulse) the electric field temporal waveform of sub-picoseconds to pico-seconds THz pulses due to the band width lack of the detection electronics, a method referred to as a Pump-Probe Method based on a mechanical time delay scanning has been utilized thus far.

Figure 10:
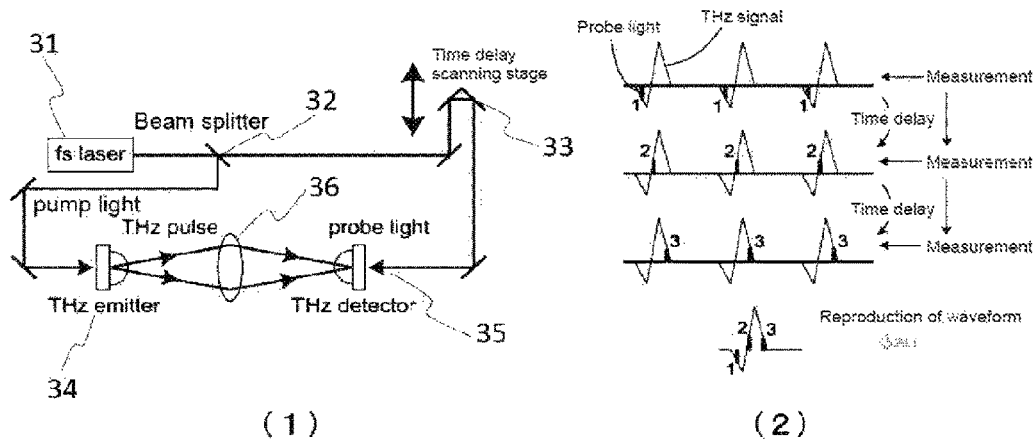
FIG. 10 An explanatory drawing of a conventional the THz-TDS equipment (A mechanically time-delay scanning, pump-probe method)

FIG. 10 shows a configuration of a typical THz-TDS device (a device employing a mechanical time delay scanning pump-probe method). The femtosecond laser light 31 is divided to the pump light for THz generation (pump light) and the probe light for THz detection (probe light) by the beam splitter 32. By making the pump light incident on the THz generation element 34 (a photo conducting antenna and so on), a THz pulse is generated. The THz pulse that propagates the free space is made incident on the THz detection element 35 (photo conducting antenna and so on). The probe light is made incident on the THz detection element 35 after adjusting the timing (optical path length) by a time delay scanning stage.

Here, as shown in FIG. 10(2), when the THz pulse and the probe light are made incident on the THz detection element with the same timing, it becomes possible to temporally cut out apart of the electric field waveform of the THz pulse by the probe light. Therefore, it becomes possible to reconstruct the THz electric field temporal waveform by cutting out the electric field temporal waveform of the THz pulse with the timing wherein the THz pulse and the probe light is overlaid while shifting the incidence timing of the probe light using the time delay scanning stage 33.

However, the device configuration employing the conventional mechanical time delay scanning pump-probe method accompanies technical difficulties for realizing the observation time window size equal to the pulse cycle that is the repetition cycle. (The time delay scanning stage 33 of more than several meters is necessary). Also, it is difficult to stabilize the cycle of the THz pulse generated by the femtosecond laser light correctly and thoroughly. For such reasons, it is not easy to implement the Fourier transform spectroscopy method of the present invention by a device using the conventional mechanical time delay scanning pump-probe method.

Figure 11:
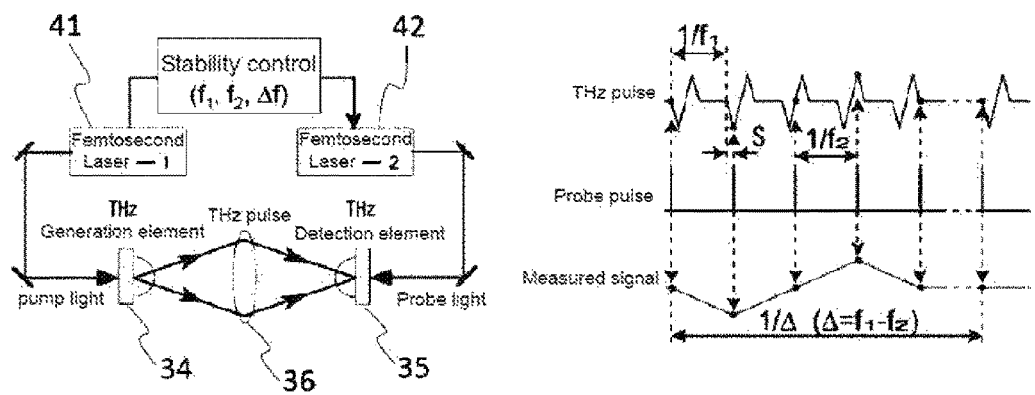
FIG. 11 An explanatory drawing of the THz-TDS principle of embodiment 1
Figure 12:
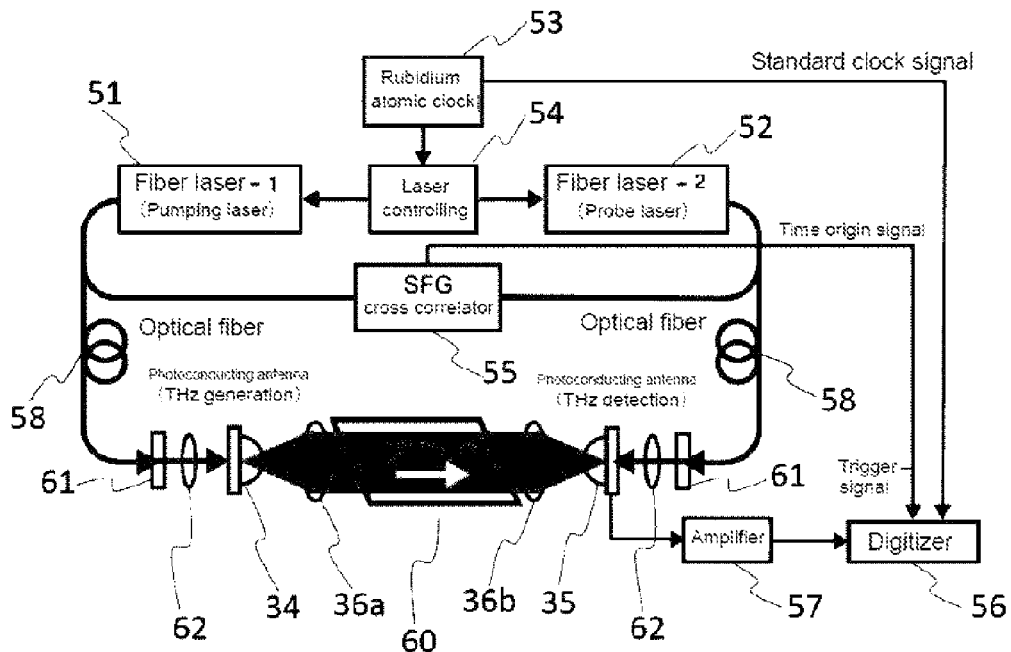
FIG. 12 A configuration of the THz-TDS of embodiment 1

Therefore, by using two femtosecond lasers (each repetition frequency of $f_1$ and $f_2$) with repetition frequencies to be controlled in advance at slightly different values as a pumping light and a probe light, and by using these lasers to the generation and detection of the THz pulse, the THz pulse wave form of picosecond order pulse ($1/f_{1\ as}$ shown FIG. 11(2)) is correctly expanded to the time scale of microsecond order ($1/\Delta(\Delta=f_1-f_2)$). As a result, the mechanical time delay scanning stage becomes unnecessary and the real time pulse measurement by an oscilloscope and so on becomes possible. By this, the limitation of the observation time window size originating to the mechanical time delay scanning is resolved and the observation time window size is expanded to the pulse cycle that is the repetition cycle. Moreover, because an arbitrary observation time window size can be set, the observation time window size can be set strictly at the same value as the pulse cycle that is the repetition cycle. Also, it is possible to perform a strict and thorough stability control of a pulse cycle by laser controlling with a micro wave atomic clock as a standard.

Moreover, further improvements of the spectral resolution and the spectral accuracy can be achieved by scanning of the plot interval, the superimposing of spectra and the complement of plot interval.

FIG. 2 shows the configuration of the THz-TDS device according to the Embodiment 1.

The pulse frequencies ($f_1$, $f_2$) of two femtosecond lasers (51, 52) (the average power of 500 mW, the central wavelength at 1550 nm and the pulse width of 50 fs) are phase locked to the rubidium atomic clock 53 so that the pulse frequencies ($f_1$, $f_2$) and the pulse frequency difference controlled by a laser control are to be slightly different. ($f_1$=250,000,000 Hz, $f_2$=250,000,050 Hz, $\Delta f = f_2 - f_2 = 50$ Hz) The fiber laser 1 (51) is used as an pumping laser and the fiber laser 2 (52) is used as a probe laser.

After converting the wavelengths of both lasers by a non-linear optical crystal, the THz-TDS optics is constructed using a photoconductive antenna (PCA) for the THz generation 34 and the THz detection 35. Here, high speed sampling is performed as shown in FIG. 11(2) wherein the timing for the THz pulse and the probe light to be overlaid on the PCA for the THz detection is automatically shifted by each pulse because the pulse cycle of the THz pulse and the probe light are slightly different to each other. As a result, the time scale of the THz pulse electric field temporal waveform in a sub-picosecond order can be expanded by an arbitrary time scale magnification power (=$f_1/\Delta f$).

The temporal waveform amplified by the amplifier 57 is acquired after the current/voltage conversion because the current signal with the time scale magnified to an RF region is output from the THz detection PCA. Also, a part of the laser light is led to a SFG (Sub Frequency Generation Light) cross correlator and the generated SFG light is used for a trigger signal of a digitizer 56 as the time origin signal. Further, the signal from the Rubidium atomic clock 53 is used as a standard clock signal of the digitizer 56.

(Usability Evaluation of the Low Pressure Gas Spectroscopy by the THz-TDS)

Next, the evaluation result of the Fourier transform spectroscopy method according to the present invention by the THz-TDS using low pressure water vapor as a sample. The water vapor in a low pressure state shows a sharp absorption line originating to a rotational transition in the THz region and the absorption line width can be adjusted by the pressure. ("the theoretical absorption line width" hereinafter) Thus, the spectral resolution was evaluated by enclosing a mixed gas of water vapor and nitrogen into a gas cell (500 mm length and 40 mm radius) and keeping the pressure low in order that the theoretical absorption line width (rotational transition $1_{10}$->$1_{01}$) around 0.557 THz becomes narrow enough.

Figure 13:
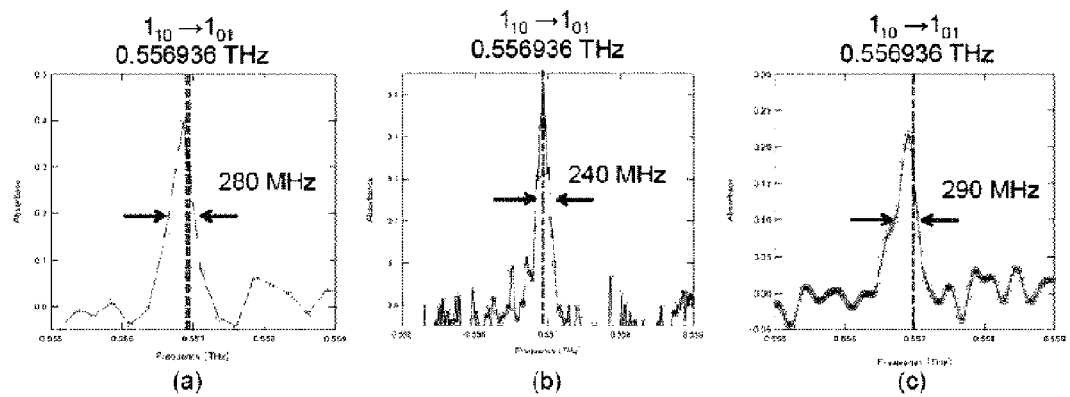
FIG. 13 An absorption spectrum of water vapor (Rotational transition $1_{10}$->$1_{01}$). (a) The present invention 1 (without spectral interleaving), (b) The present invention 2 (with spectral interleaving), (c) The previous method (the zero filling method)

First, a water vapor sample (Water vapor 170 Pa; Nitrogen 3200 Pa) with the theoretical absorption line width set at 250 MHz was measured. FIG. 13(a) shows an absorption spectrum under a condition wherein the pulse cycle that is a repetition cycle and the observation time window size strictly coincide. (The linewidth of the observed absorption spectrum is called ("an observation absorption linewidth" hereinafter). FIG. 13(a) is equivalent to FIG. 7(a) described earlier. The absorption spectrum constitutes plots of an interval equal to the pulse frequency (=250 MHz) and the observation absorption linewidth is slightly widened from the theoretical absorption linewidth. This is due to the fact that detailed spectral shape is not acquired because the plot distribution is rough compared with the theoretical absorption linewidth.

Next, a fine spectrum obtained by spectral overlaying of the serially scanned spectra to fill in the gap between plots is shown in FIG. 13(b). The FIG. 13(b) is equivalent to what is shown on the right side of FIG. 9 mentioned earlier. An observed absorption linewidth of about 250 MHz is obtained reflecting a finer spectral shape.

A spectrum obtained by the zero-filling method often used as a conventional method which is a method to increase the spectral number of data obtained by the FT-IR and so on is shown as comparison data in FIG. 13(c). It is understood that the spectral shape is almost identical to the one in FIG. 13(a), with the spectral resolution not being improved intrinsically, though the number of plot is remarkably increased (10 times larger than the one in FIG. 13(a)) as shown in FIG. 13(c). Also, it can be confirmed that the spectral accuracy of the spectrum in FIG. 13(b) is improved when a comparison is made with the spectral database value (0.556946 THz) of NASA (National Aeronautical and Space Administration) for the rotational transition $1_{10}$->$1_{01}$.

Next, the necessity for letting the repetition cycle and the observation time window size strictly agree is confirmed. First, the pressure is controlled for the theoretical absorption linewidth to become 10 MHz so that the absorption relaxation phenomenon by water vapor lasts longer than the repetition cycle (4 ns). A gas mixture of water vapor and Nitrogen (water vapor 6 Pa; Nitrogen 140 Pa) was used as a sample of water vapor in a low pressure state. The relaxation of the absorption phenomenon of the theoretical absorption linewidth 10 MHz proceeds with the relaxation time of 100 ns which is a reciprocal of the theoretical absorption linewidth. The relaxation time 100 ns corresponds to 25 cycles of a repetition cycle (4 ns).

Figure 9:
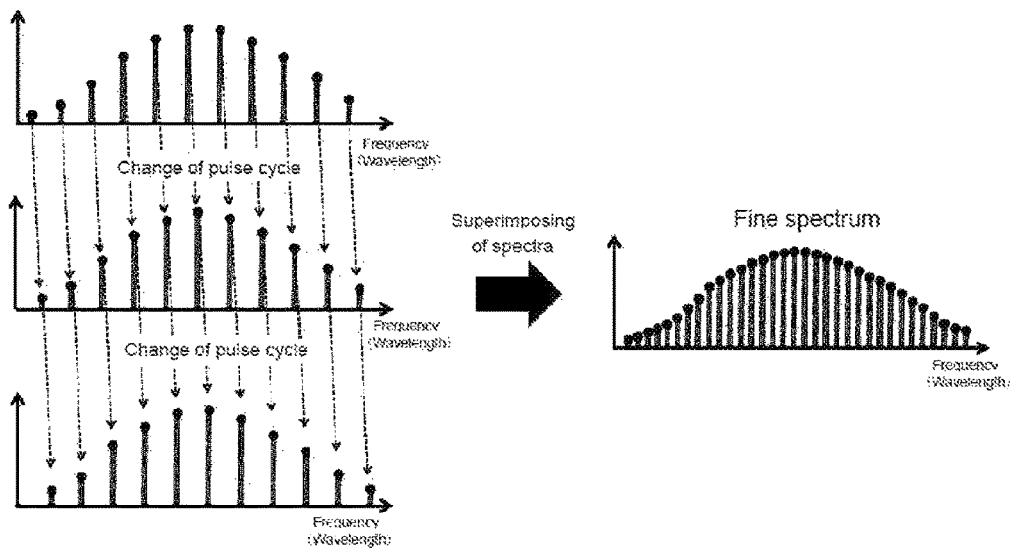
Figure 14:
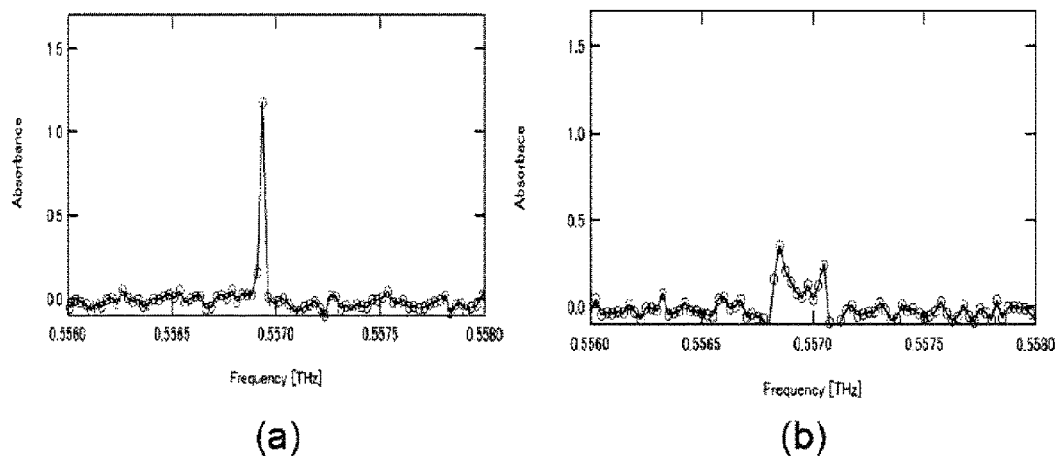
FIG. 14 An absorption spectrum in a case where an absorption relaxation phenomenon is longer than a repetition period. (a) Observation time window size=1 period, (b) Observation time window size=0.99995 period, and (c) Observation time window size=1 period achieved by connecting the temporal data for 0.9995 period and the null data for 0.0005 period FIG. 15 An absorption spectrum in a case where an absorption relaxation phenomenon is shorter than a repetition period. (a) Observation window=1 period, (b) Observation window=0.99995 period FIG. 16 A relation between total gas pressure and the pressure-broadening absolution linewidth in the present invention (without spectral interleaving), the present invention (with spectral interleaving) and the convention method (the zero-filling method)

Under the condition mentioned above, fine absorption spectra were acquired for the cases wherein the observation time window size=1 cycle and the observation time window size=0.99995 (refer to the right side of FIG. 9). The measurement result is shown in FIG. 14. When the observation time window size=1 cycle, a sharp and symmetrical absorption spectrum is acquired and the observation absorption linewidth is 29 MHz (Refer to FIG. 14(a). An error from the theoretical absorption linewidth (10 MHz) is due to instability of sample gas pressure. On the other hand, a distorted spectral waveform was observed when the observation time window size=0.99995 cycles (Refer to FIG. 14(b)). This is presumed to be due to generation of a temporal discontinuity connection.

Figure 15:
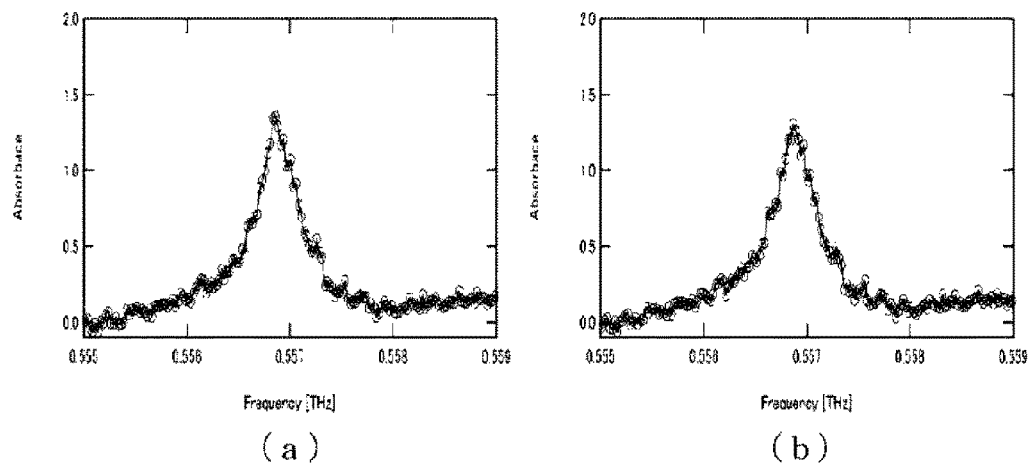

A similar measurement was performed by setting the continuity time of absorption relaxation phenomenon shorter than the repetition cycle for obtaining comparison data. Here, the pressure was controlled (Water vapor 1000 Pa; Nitrogen 3500 Pa) to let the theoretical absorption linewidth be 500 MHz and also let the duration of the relaxation phenomenon be 2 ns which is a half of the repetition cycle (4 ns). The measurement result is shown in FIG. 15. Observation absorption linewidths almost equal to the theoretical absorption linewidths were obtained by the measurement results for the cases wherein the observation time window size=1 cycle (Refer to FIG. 15 (a)) and for the case wherein the observation time window size=0.99995 (Refer to FIG. 15(b)). This means that a temporal discontinuous connection is included in the observation temporal waveform even in the case of FIG. 15(b) wherein the observation time window size=0.99995 because the continuation time of the absorption relaxation phenomenon is shorter than the repetition cycle. These results show that strict matching of the repetition cycle and the observation time window size is extremely important when the relaxation phenomenon is longer than the repetition cycle for the Fourier spectroscopy method of the present invention.

Next, the absorption spectra were measured while the theoretical absorption linewidth was changed by a pressure control, to evaluate the achievable spectral resolution.

Figure 16:
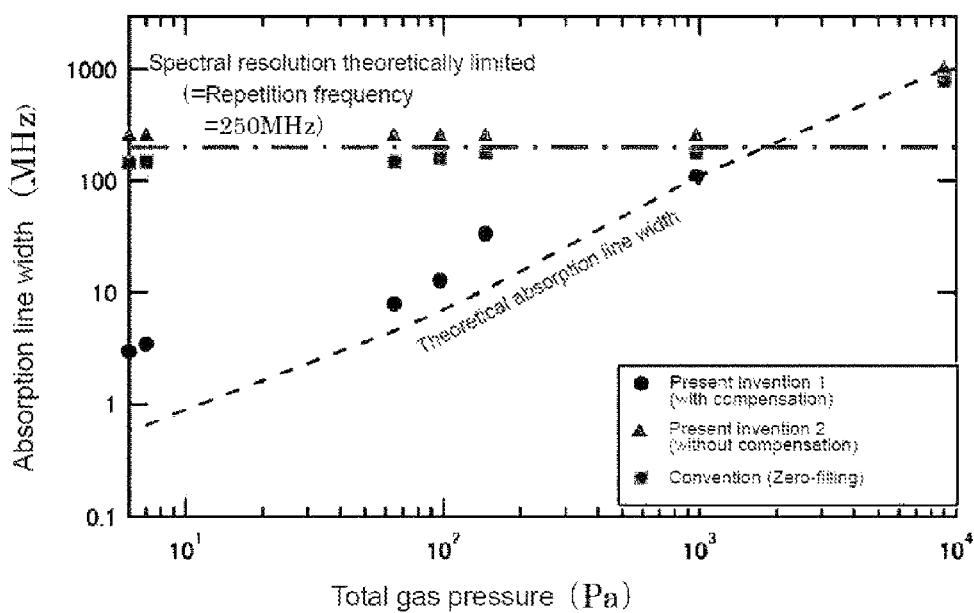

FIG. 16 shows the comparison results of the pressure dependence of the theoretical absorption linewidth and the observation absorption linewidth for 3 cases that are this invention (without compensation of discrete distribution spectral interval), this invention (with compensation of discrete distribution spectral interval) and the conventional method (the zero-filling method). Here, the dotted line represents a theoretical line of the theoretical absorption linewidth.

The observation absorption width remained at about 250 MHz under the pressure lower than 1 kPa while the observation absorption width decreased with the decrease of the pressure down to near 1 kPa according to the present invention (without compensation of discrete distribution spectral interval) and the conventional method (Zero-filling method). This shows that the observation absorption linewidth is observed as extended due to the spectral resolution limit of the device, not reflecting the theoretical absorption line width. Namely, the spectral resolutions of the present invention (without compensation of discrete distribution spectrum) and the conventional method (Zero-filling method) are shown to be 250 MHz which is the plot interval (repetition frequency), a theoretically limited spectral resolution.

On the other hand, the observation absorption linewidth according to the present invention (with a compensation of a discrete distribution spectral interval) similarly changes as the theoretical absorption linewidth. For example, in the experiment of the lowest gas pressure of 5 Pa, the observed spectral width is 3 MHz which substantially exceeds the repetition frequency (250 MHz) which is the theoretically limited spectral resolution. Also, the discrepancy from the theoretical curve in the low pressure region is due to the instability of the sample gas pressure, not due to the spectral resolution limit of the device of the present invention. In the Fourier transform spectroscopy method of the present invention, the infinitesimal spectral resolution (the infinite spectral resolving power) is theoretically achievable. However, the limitation of spectral resolution is practically determined by the stability of the repetition frequency and so on.

[Embodiment 2]

Figure 17:
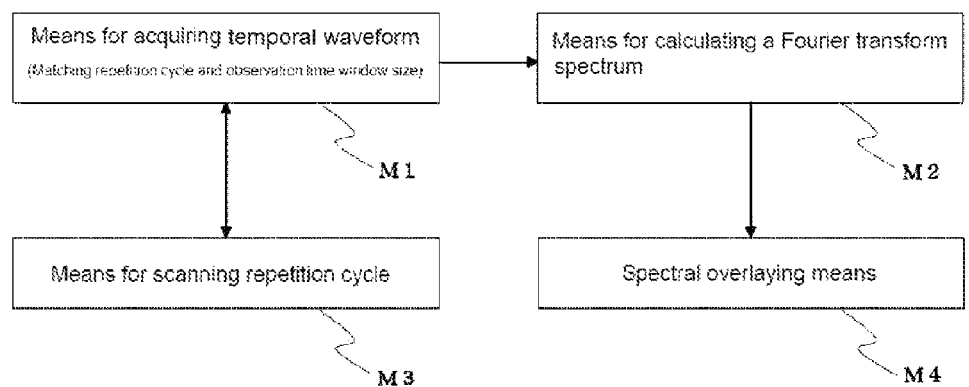
FIG. 17 A functional block diagram of the Fourier transform spectroscopic program FIG. 18 A processing flow of the Fourier transform spectroscopic program FIG. 19 An internal structure of a computer hardware FIG. 20 An amplitude spectrum showing a fine structure of acetonitrile gas FIG. 21 An absorption spectrum in the region of 0.6~0.7 THz obtained by changing the repetition frequency FIG. 22 An absorption spectrum regarding the rotational transition J=34~35 (near 0.64 THz) obtained by changing the repetition frequency FIG. 23 An absorption spectrum around 0.6432 THz obtained by changing the repetition frequency

The Fourier transform measurement program is explained in Embodiment 2. FIG. 17 shows a functional block diagram of the Fourier transform spectral measurement program.

The Fourier transform spectral measurement program of Embodiment 2 is a program which observes the periodical and repetitive phenomena and makes a computer execute the means from M1) thorough M4) below.

(M1) Means for Acquiring Temporal Waveforms

A temporal waveform is acquired by matching the repetition cycle of the phenomenon and the time width for observing the temporal waveform of the phenomenon (the observation time window size).

(M2) Means for Calculating a Fourier Transform Spectrum

A Fourier transform spectrum is calculated from the temporal waveform acquired by the temporal waveform acquiring means by M1 above.

(M3) Means for Scanning Repetition Cycle

The repetition frequency is scanned (the repetition frequency is changed) for compensating the gap of the discrete distribution spectrum.

(M4) Spectral Overlaying Means

First, temporal waveforms of phenomena with the repetition cycles changed by the means of M3 above for scanning the repetition cycle are acquired by the means of M1 above for acquiring temporal waveforms and then a fine spectrum with the gap of the discrete distribution spectrum compensated is obtained after overlaying each spectrum obtained by the means of M2 above for calculating a Fourier transform spectrum, that is to say each spectrum of a different repetition cycle.

Figure 18:
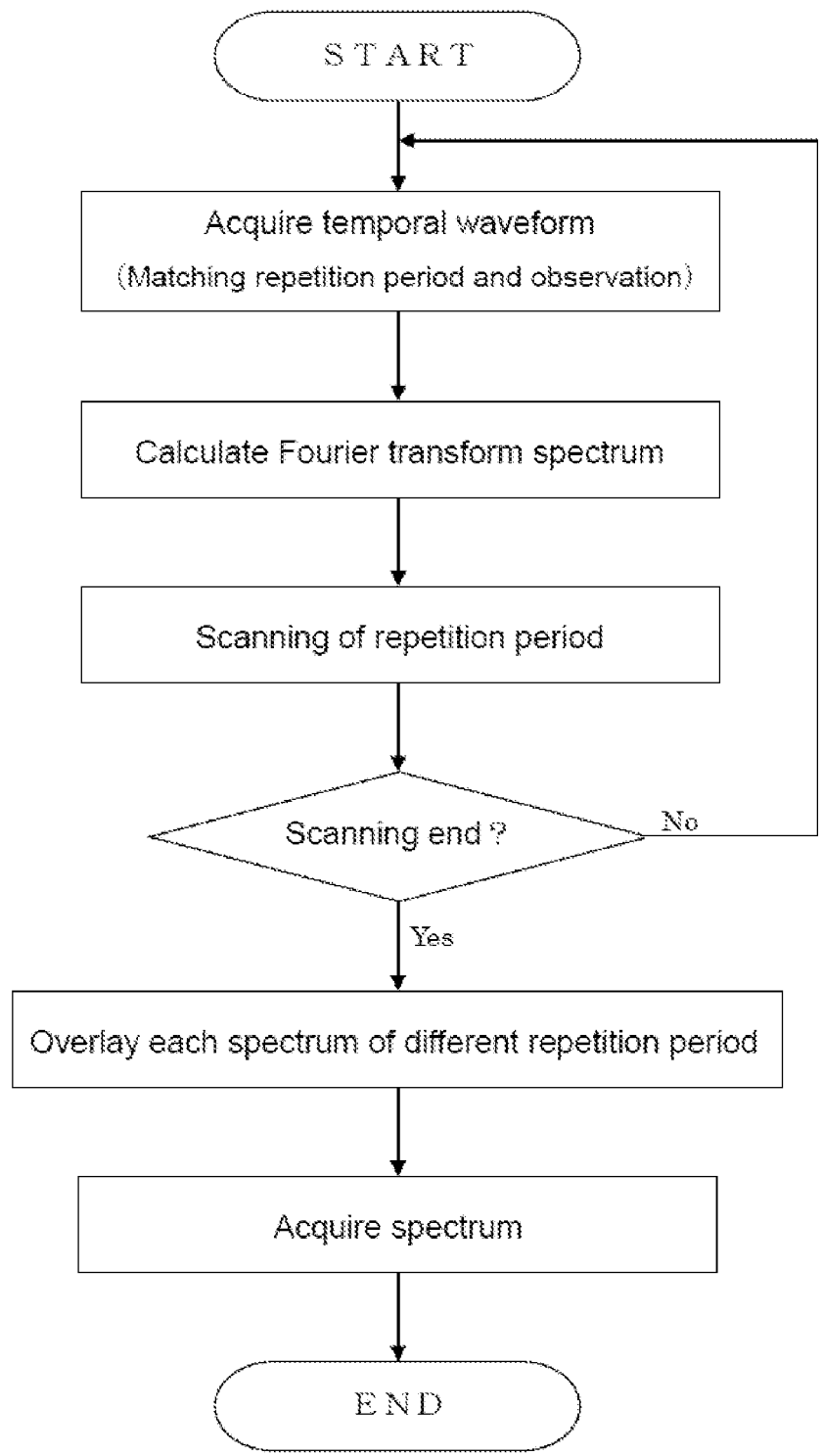

And, FIG. 18 shows the process flow of the Fourier transform spectral measurement program.

The Fourier transform spectral measurement program acquires the temporal waveform as it is by matching the periodical and repetitive phenomenon with the observation time window size to observe the periodical and repetition phenomena. And, the Fourier transform spectrum is calculated from the acquired temporal waveform. And the repetition frequency is scanned for compensating the gap of the discrete distribution spectrum. The scanning is performed as many times as needed to supplement the gaps of the discrete distribution spectrum.

And the time waveform of the phenomenon under the change of the repetition period is acquired by the scanning of the repetition period and each spectrum (each spectrum of different repetition period) obtained by the Fourier transform of thus acquired temporal waveform is overlaid each other to acquire the fine spectrum with the gaps of the discrete distribution spectrum are supplemented.

Figure 19:
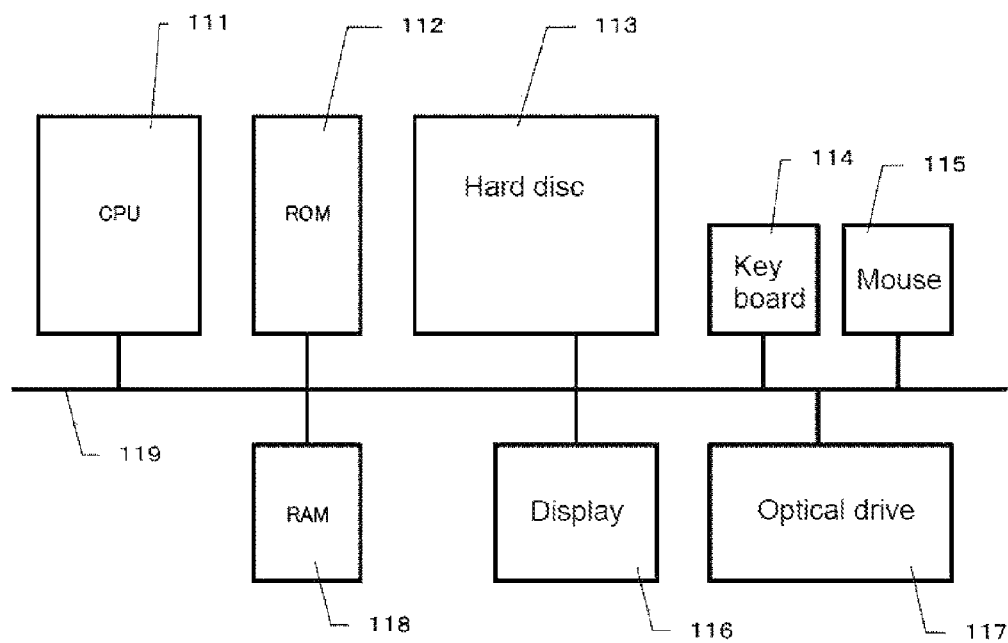

FIG. 19 shows the internal configuration of a hardware that executes the Fourier transform spectroscopic measurement program. In FIG. 19, the inner configuration of the computer hardware furnishes the CPU 111, the ROM 112, the hard disc 113, the keyboard 114, the mouse 115, the display 116, the optical drive 117 and the RAM 118 and these are all connected to the system bus 119. The RAM 118 temporally stores the command of the Fourier transform spectroscopic measurement program and provides a temporal storage space. The hard disc 113 stores the Fourier transform spectroscopic measurement program, the system program and the data. The keyboard 114 and the mouse 115 receive commands from a computer operator. The display 116 displays output data by the Fourier transform spectroscopic measurement program. Note that the computer may include a network interface (not illustrated) for the connection with a network.

The Fourier transform spectroscopic measurement program can be operated by sharing computer hardware (CPU, ROM, Hard disc and so on) prepared as standard equipment and can be mounted as an additional option of the standard program in Fourier transformation spectroscopic devices such as the nuclear magnetic resonance spectroscopic (NMR) device, the nuclear magnetic resonance imaging (MRI) device, the terahertz time domain spectroscopic (THz-TDS) device, the Fourier transform infrared spectroscopic (FT-IR) device, the Fourier transform mass spectrometric analysis (FT-MS), the Fourier transform light spectrum analyzer and the Fourier transform spectrum analyzer.

[Embodiment 3]

In Embodiment 1 mentioned above, the usefulness evaluation result of the Fourier transform spectroscopy method according to the present invention was explained by using low pressure water vapor as a sample in the case of the THz-TDS.

In Embodiment 3, usefulness of the Fourier transform spectroscopy method according to the present invention is explained by the measurement of the acetonitrile (CH$_3$CN) absorption line in the case of the THz-TDS.

Acetonitrile is one of the interstellar substances and the research to measure the absorption line of Acetonitrile is regarded to be important for the purpose of knowing the physical state of the universe in the field of the space astronomy. Acetonitrile is composed of a symmetrical top-type molecule and the absorption line frequency ν is expressed by the Equation (8) as below.
[Equation 8]

$$\nu = 2B(J+1) - 4D_J(J+1)^3 - 2D_{JK}(J+1)K^2 \qquad (8)$$

Here, B is the rotational constant around the axis of symmetry, D$_J$ and D$_{JK}$ are the centrifugal strain constants by the molecular rotation, J is the total angular momentum rotational quantum number and K is the molecular symmetry direction rotational quantum number.

Because D$_J$ and D$_{JK}$ are very small compared with the coefficient B, the absorption line appears with an equal interval of the frequency 2B (=18.4 GHz) when observed over a wide range and the absorption line frequency ν is expressed by the Equation (9) as shown below.
[Equation 9]

$$\nu \approx 2B(J+1) \qquad (9)$$

Further, the microstructure by the quantum number K begins to appear when observed over a narrower range. It has been difficult to observe these at a time using the conventional Terahertz Spectroscopic device. For this reason, it has been necessary to employ a broadband THz-TDS device for observing the structure by the quantum number J and to employ a high resolution Continuous-Wave (CW)-THz spectroscopic device for observing a microstructure by the quantum number K. When the Fourier transform spectroscopy method according to the present invention with the dynamic range (the ratio of the spectral resolution and the spectral coverage) extremely high, it is possible to observe these two kinds of structures by one Terahertz spectroscopic device.

In the current Embodiment, the measurement was performed by setting the pressure at 30 Pa to prevent the microstructure of gaseous Acetonitrile to be overlaid by pressure broadening.

The mode synchronous frequency was changed 20 times so that the plot interval becomes 12.5 MHz each for observing the microstructure in the vicinity of the J=34·35 transition.

Figure 20:
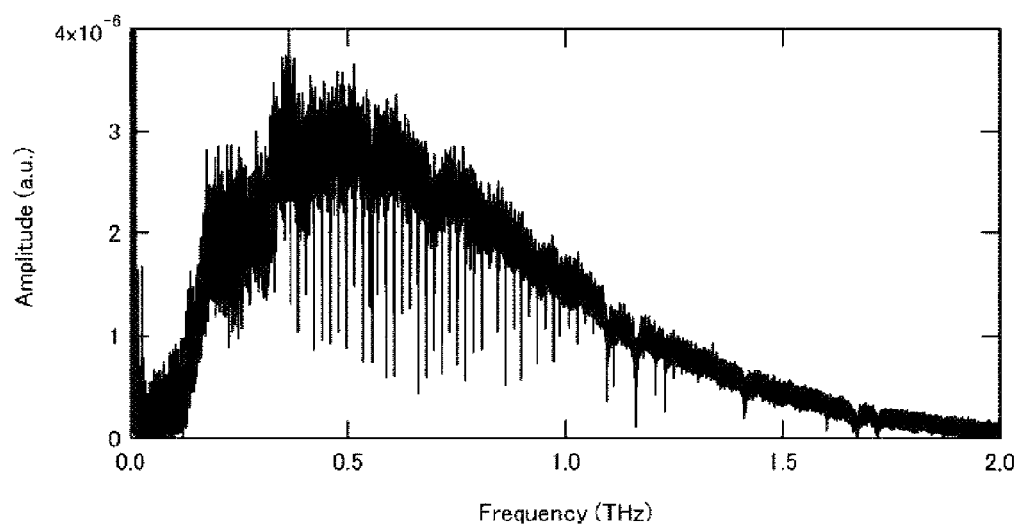

The amplitude spectrum of the total spectrum is shown in FIG. 20. The cyclic absorption line of an Acetonitrile molecule can be confirmed near the 0.3~0.1 THz region.

Figure 21:
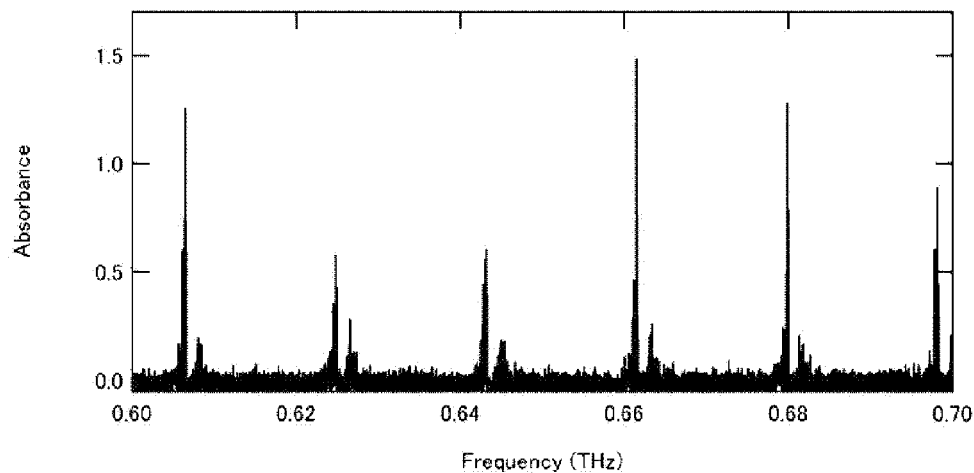

Next, an absorption spectrum was calculated. The absorption spectrum in the region of 0.6 to 0.7 THz is shown in FIG. 21. It can be confirmed that the 6 absorption lines of Acetonitrile exist with an interval of about 18.4 GHz which is almost the same as the predictive value.

Figure 22:
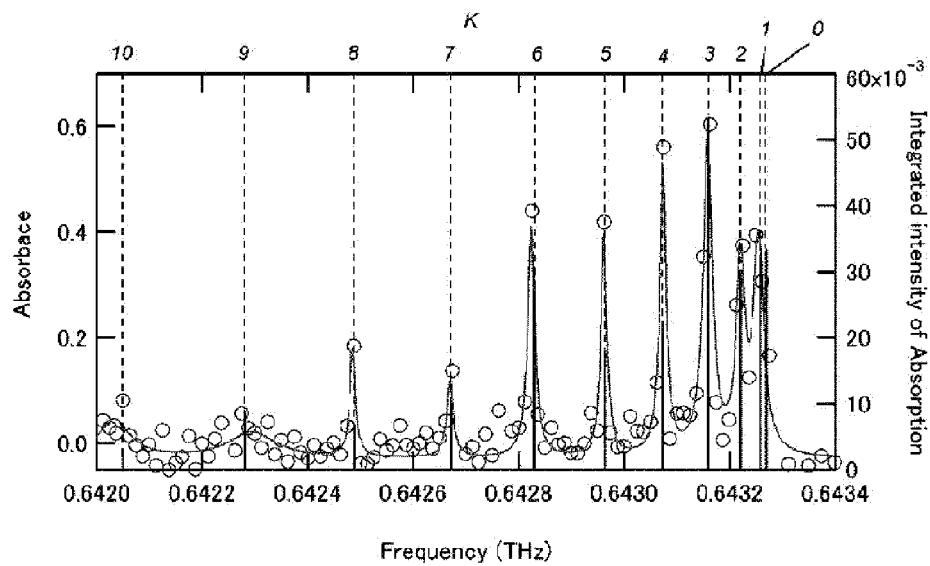

Further, an absorption spectrum with the vicinity of the J=34~35 transition (near 0.64 THz) enlarged is shown in FIG. 22. FIG. 22 shows a curve with each plot (shown by ○ in the figure) thereon the curve fitting by the Lorentz function is performed. Also, the bar depicted on the extension of dotted lines for K=0 to 10 shows the absolute frequency and the integration intensity of Acetonitrile quoted from the NASA (National Aeronautics and Space Administration) database.

FIG. 22 shows that the microstructure by the quantum number K can be confirmed and K=2 to 10 can be identified.

On other hand, two absorption lines K=0 and 1 with a frequency interval of 12.3 MHz cannot be separated/identified under the experimental condition of the 12.5 MHz spectral plot interval. In FIG. 22, the mode-locked frequency is further changed so that the spectral spot interval is shifted by 1.25 MHz for 20 times in the vicinity of 0.6432 THz to identify two absorption lines K=0 and 1 that cannot be separated/identified.

Figure 23:
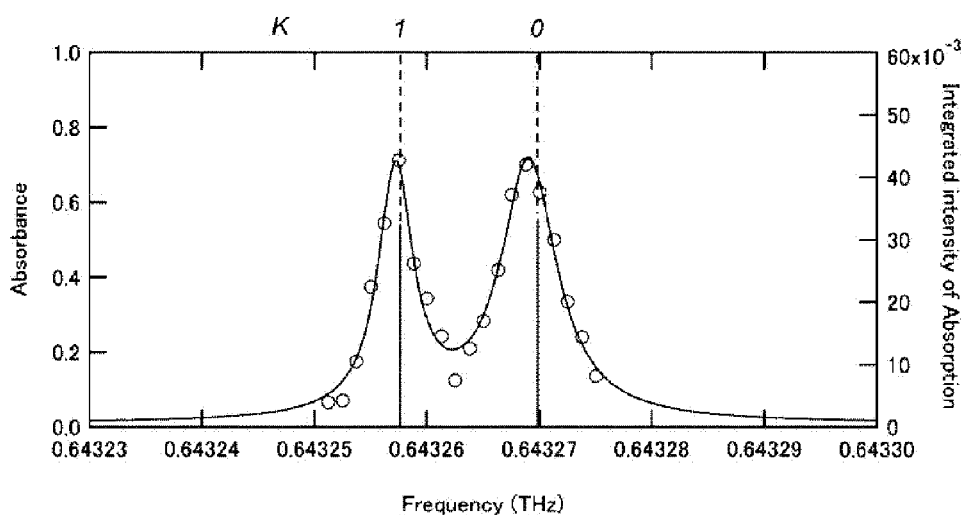

FIG. 23 shows an absorption spectrum with the vicinity of 0.6432 THz enlarged, which is obtained by overlaying multiple discrete distribution spectra by changing the mode-locked frequency. It is shown in FIG. 23 that the two absorption lines K=0, 1 with the frequency interval of 12.3 MHz are clearly distinguished. The result that the narrower the spectral plot interval becomes, the spectral resolution becomes better, means that each spectral plot is attaining the infinitesimal spectral resolution (the infinite spectral resolving power) according to the present invention.

Also, the spectral accuracy coincides within half (0.625 MHz) of the frequency scanning step of 1.25 MHz meaning that high accuracy is obtained.

As was explained above, the method of being the Fourier transform spectroscopy method according to the present invention, wherein changing the mode synchronizing frequency, and further superimposing multiple discrete distribution spectra and then complementing the gap of each plot of discrete distribution thus acquired, combines the broadband characteristics of the THz-TDS and the high spectral resolution of the CW-THz spectroscopy method and further it will be understood that the spectral accuracy is guaranteed by a microwave frequency standard.

(Other Embodiments)

In the Embodiment described above, an example of applying the Fourier Transform spectroscopy method to the terahertz time region spectroscopic device (THz-TDS) was explained. It should be noted that the Fourier transform spectroscopy method can be further applied to and the Fourier transform spectroscopic measurement program can be mounted on the nuclear magnetic resonance spectroscopic (NMR) device, the nuclear magnetic resonance imaging (MRI) device, the Fourier transform infrared spectroscopic (FT-IR) device, the Fourier transform mass spectrometric analysis (FT-MS), the Fourier transform light spectrum analyzer and the Fourier transform spectrum analyzer.

INDUSTRIAL APPLICABILITY

The present invention can be applied to the Fourier transform spectroscopic devices such as such as the terahertz time domain spectroscopic (THz-TDS) device, the nuclear magnetic resonance spectroscopic (NMR) device, the nuclear magnetic resonance imaging (MRI) device, the Fourier transform infrared spectroscopic (FT-IR) device, the Fourier transform mass spectrometric analysis (FT-MS), the Fourier transform light spectrum analyzer and the Fourier transform spectrum analyzer.

DESCRIPTION OF SYMBOLS 10 to 13 Temporal waveform
20 Frequency signal
31, 41, 42 Femtosecond laser
32 Beam splitter
33 Time delay scanning stage
34 THz generation device
35 THz detection device 36, 36a, 36b Collecting lens
51, 52 Fiber laser
53 Rubidium atomic clock
54 Laser control equipment
55 SFG inter correlator
56 Digitizer
57 Amplifier
58 Optical fiber
60 Gas cell
61 Optical fiber end
62 Collecting lens

What is claimed is:

1. A Fourier transform spectroscopy method including a Fourier transform frequency analysis method, for observing a periodical and repetitive phenomenon, the method comprising:
  acquiring a temporal waveform by matching a repetition period of a phenomenon with an observation time window size T for observing a temporal waveform of a phenomenon;
  obtaining a discrete distribution spectrum with a frequency interval equal to a reciprocal of said observation time window size T, by a Fourier transform of an acquired time waveform; and
  holding the formula $f_n=n/T$ true for each plot of said discrete distribution spectrum, with $f_n$ as a frequency of each plot and integer n as an order of plot;
  wherein the temporal waveform is acquired by observing a phenomenon within a time window size shorter than said repetition period, introducing null data for the acquired temporal waveform data to be matched to the repetition period and acquiring a temporal waveform matching with the repetition period, instead of matching the repetition period of said phenomenon with said observation time window size T.

2. The Fourier transform spectroscopy method according to claim 1, wherein said repetition period is stabilized by referencing a frequency standard.

3. The Fourier transform spectroscopy method according to claim 1, further comprising:
  acquiring a discrete distribution spectrum by a Fourier transform of a digitized temporal waveform data in 1 period of said repetition period, said discrete distribution spectrum acquired at least in part either by (a) digitizing a temporal waveform data with a time interval of 1/d of said repetition period where d is an integer, or (b) setting the period of said repetition phenomenon at an integer multiple of digitized time interval of temporal waveform data.

4. The Fourier transform spectroscopy method according to claim 1, further comprising:
  applying said method in conducting a terahertz time-domain spectroscopy method (THz-TDS);
  employing 2 femtosecond lasers with different laser pulse repetition mode-locked frequencies as light sources for a terahertz time-domain spectroscopy method;
  each mode-locked frequency of said 2 femtosecond lasers being stabilized by referencing a frequency standard and further, 2 femtosecond lasers being independently controlled so that the mode-locked frequency difference is kept at a constant value;
  optical output of one femtosecond laser being used as a pumping light for THz generation, and optical output of the other femtosecond laser being used as a probe pulse light for THz detection; and
  stabilizing said repetition period.

5. The Fourier transform spectroscopy method according to claim 1, further comprising;
  applying said method in conducting a Fourier transform infrared spectroscopy method (FT-IR);
  employing 2 femtosecond lasers with different laser pulse repetition mode-locked frequencies as light sources for a Fourier transform infrared spectroscopy method;
  each mode-locked frequency and carrier-envelope-offset frequency of said 2 femtosecond lasers being stabilized by referencing a frequency standard and further, 2 femtosecond lasers being independently controlled so that the mode-locked frequency difference is kept at a constant value;
  optical output of one femtosecond laser being used as an IR light for sample measurement and optical output of the other femtosecond laser being used for a local oscillator light in heterodyne interferometer; and
  stabilizing said repetition period.

6. The Fourier transform spectroscopy method according to claim 1, further comprising using at least one of the following as a Fourier transform spectroscopic device: a nuclear magnetic resonance spectroscopic (NMR) device, a nuclear magnetic resonance image (MRI) device, a terahertz time-domain spectroscopic (THz-TDS) device, a Fourier transform infrared spectroscopic (FT-IR) device, a Fourier transform mass spectroscopic (FT-MS) device, or an optical or electrical Fourier transform spectrum analyzer.

7. A Fourier transform spectroscopy method including a Fourier transform frequency analysis method, for observing a periodical and repetitive phenomenon, the method comprising:
  acquiring a temporal waveform by matching a repetition period of a phenomenon with an observation time window size T for observing a temporal waveform of a phenomenon;
  obtaining a discrete distribution spectrum with a frequency interval equal to a reciprocal of said observation time window size T by a Fourier transform of an acquired time waveform;
  holding the formula $f_n=n/T$ true for each plot of said discrete distribution spectrum, with $f_n$ as a frequency of each plot and integer n as an order of plot;
  changing said repetition period;
  acquiring a discrete distribution spectrum of a temporal waveform acquired after changing the repetition period; and
  superimposing multiple discrete distribution spectra of different repetition periods.

8. The Fourier transform spectroscopy method according to claim 7, wherein said repetition period is stabilized by referencing a frequency standard.

9. The Fourier transform spectroscopy method according to claim 7, further comprising:
  acquiring a discrete distribution spectrum by a Fourier transform of a digitized temporal waveform data in 1 period of said repetition period, said discrete distribution spectrum acquired at least in part either by (a) digitizing a temporal waveform data with a time interval of 1/d of said repetition period where d is an integer, or (b) setting the period of said repetition phenomenon at an integer multiple of digitized time interval of temporal waveform data.

10. The Fourier transform spectroscopy method according to claim 7, further comprising:
  applying said method in conducting a terahertz time-domain spectroscopy method (THz-TDS);

employing 2 femtosecond lasers with different laser pulse repetition mode-locked frequencies as light sources for a terahertz time-domain spectroscopy method;

each mode-locked frequency of said 2 femtosecond lasers being stabilized by referencing a frequency standard and further, 2 femtosecond lasers being independently controlled so that the mode-locked frequency difference is kept at a constant value;

optical output of one femtosecond laser being used as a pumping light for THz generation, and optical output of the other femtosecond laser being used as a probe pulse light for THz detection; and stabilizing said repetition period.

11. The Fourier transform spectroscopy method according to claim 7, further comprising;

applying said method in conducting a Fourier transform infrared spectroscopy method (FT-IR);

employing 2 femtosecond lasers with different laser pulse repetition mode-locked frequencies as light sources for a Fourier transform infrared spectroscopy method;

each mode-locked frequency and carrier-envelope-offset frequency of said 2 femtosecond lasers being stabilized by referencing a frequency standard and further, 2 femtosecond lasers being independently controlled so that the mode-locked frequency difference is kept at a constant value;

optical output of one femtosecond laser being used as an IR light for sample measurement and optical output of the other femtosecond laser being used for a local oscillator light in heterodyne interferometer; and stabilizing said repetition period.

12. The Fourier transform spectroscopy method according to claim 7, further comprising using at least one of the following as a Fourier transform spectroscopic device: a nuclear magnetic resonance spectroscopic (NMR) device, a nuclear magnetic resonance image (MRI) device, a terahertz time-domain spectroscopic (THz-TDS) device, a Fourier transform infrared spectroscopic (FT-IR) device, a Fourier transform mass spectroscopic (FT-MS) device, or an optical or electrical Fourier transform spectrum analyzer.

13. A Fourier transform spectroscopic device for observing a periodical and repetitive phenomenon, the device comprising:

means for acquiring a temporal waveform by matching a repetition period of a phenomenon with an observation time window size T for observing a temporal waveform of a phenomenon;

means for obtaining a discrete distribution spectrum with a frequency interval equal to a reciprocal of said observation time window size T by a Fourier transform of an acquired time waveform;

means for changing said repetition period;

means for overlaying multiple discrete distribution spectra of different repetition periods;

wherein each plot of said discrete distribution spectrum is held true for the formula $f_n = n/T$, where $f_n$ is a frequency of each plot and integer n is an order; and the spectral resolution of the acquired discrete distribution spectrum becoming infinitesimal (the spectral resolving power becoming infinite) in a case of an observed phenomenon with the relaxation time being longer than said repetition period, and consequently the spectral accuracy being improved.

14. The Fourier transform spectroscopic device according to claim 13, configured for conducting a terahertz time-domain spectroscopy method (THz-TDS), wherein:

the device is equipped with 2 femtosecond lasers with different laser pulse repetition mode-locked frequencies as light sources for a terahertz time-domain spectroscopy method;

each mode-locked frequency of said 2 femtosecond lasers is stabilized by referencing a frequency standard and further, 2 femtosecond lasers are independently controlled so that the mode-locked frequency difference is kept at a constant value;

optical output of one femtosecond laser being used as a pumping light for THz generation, and optical output of the other femtosecond laser being used as a probe pulse light for THz detection; and said repetition cycle is stabilized.

15. The Fourier transform spectroscopic device according to claim 13, configured for conducting a Fourier transform infrared spectroscopy method, wherein:

the device is equipped with 2 femtosecond lasers with different laser pulse repetition mode-locked frequencies as light sources for a Fourier transform infrared spectroscopy method;

each mode-locked frequency and carrier-envelope-offset frequency of said 2 femtosecond lasers is stabilized by referencing a frequency standard and further, 2 femtosecond lasers being independently controlled so that the mode-locked frequency difference is kept at a constant value;

optical output of one femtosecond laser being used as an IR light for sample measurement and optical output of the other femtosecond laser being used for a local oscillator light in heterodyne interferometer; and said repetition period is stabilized.

16. A computer storage storing a Fourier transform spectroscopic measurement program for observing a periodical and repetitive phenomenon and for making a computer to function according to steps comprising:

acquiring a temporal waveform by matching a repetition period of a phenomenon with an observation time window size T for observing a temporal waveform of the phenomenon;

obtaining a discrete distribution spectrum with a frequency interval equal to a reciprocal of said observation time window size T by a Fourier transform of an acquired time waveform;

changing said repetition period;

overlaying multiple discrete distribution spectra with different repetition periods;

holding $f_n = n/T$ true for each plot of said discrete distribution spectrum, with $f_n$ being a frequency of each plot and integer n being an order; and wherein the spectral resolution of the acquired discrete distribution spectrum approaches an infinitesimal value and the spectral resolving power becomes unboundedly large in a case of observed phenomenon with the relaxation time being longer than said repetition period, and the spectral accuracy being improved.

* * * * *